(12) United States Patent
Wolfe et al.

(10) Patent No.: US 8,882,677 B2
(45) Date of Patent: Nov. 11, 2014

(54) MICROPHONE FOR REMOTE HEALTH SENSING

(71) Applicant: Empire Technology Development, LLC, Wilmington, DE (US)

(72) Inventors: Andrew Wolfe, Los Gatos, CA (US); Thomas Martin Conte, Decatur, GA (US)

(73) Assignee: Empire Technology Development LLC, Wilmington, DE (US)

(*) Notice: Subject to any disclaimer, the term of this patent is extended or adjusted under 35 U.S.C. 154(b) by 0 days.

(21) Appl. No.: 14/030,884

(22) Filed: Sep. 18, 2013

(65) Prior Publication Data
US 2014/0018703 A1    Jan. 16, 2014

Related U.S. Application Data

(62) Division of application No. 12/392,913, filed on Feb. 25, 2009.

(51) Int. Cl.
*A61B 5/02* (2006.01)
*A61B 5/04* (2006.01)
*A61N 1/00* (2006.01)

(52) U.S. Cl.
USPC ........... 600/528; 600/509; 600/514; 600/516; 607/60

(58) Field of Classification Search
USPC ................ 600/509, 514, 516, 528; 607/60
See application file for complete search history.

(56) References Cited

U.S. PATENT DOCUMENTS

| | | |
|---|---|---|
| 5,444,786 A | 8/1995 | Raviv |
| 5,555,891 A | 9/1996 | Eisenfeld |
| 5,774,055 A | 6/1998 | Pomerantz |
| 5,853,005 A * | 12/1998 | Scanlon ............... 600/459 |
| 6,321,197 B1 | 11/2001 | Kushner et al. |
| 6,480,733 B1 * | 11/2002 | Turcott ............... 600/516 |
| 6,544,199 B1 | 4/2003 | Morris |
| 6,553,256 B1 | 4/2003 | Jorgenson et al. |
| 6,575,902 B1 | 6/2003 | Burton |
| 6,611,783 B2 | 8/2003 | Kelly et al. |

(Continued)

FOREIGN PATENT DOCUMENTS

| | | |
|---|---|---|
| JP | H07-99329 A | 4/1995 |
| KR | 1020000003827 | 1/2000 |

(Continued)

OTHER PUBLICATIONS

"Snoring and Sleep Apnea", Health Wellness Resources, Information & Resources for Sleep Apnea: Chemistry Behind Sleep Apnea and Snoring (2007), http://wayback.archive.org/web/20071001000000*/http://www.healthwellness1.com/sleepapnea/snoring_and_sleep_apnea.php.

*Primary Examiner* — Nicole F Lavert
(74) *Attorney, Agent, or Firm* — Dorsey & Whitney LLP

(57) ABSTRACT

A health sensing device is described for placement on a user. The device may include a sensor, a filter, and a transmitter. The sensor is configured to sense one or more factors relating to an indicator of a health related condition or occurrence. The filter is configured to evaluate a signal from the sensor and determine if the indicator has been detected. The transmitter is arranged for initiating a transmission based on a signal from the filter. The sensor can include one or more microphone devices, accelerometers, and/or MEMS devices. A method of monitoring a user for a health related condition is also described.

17 Claims, 9 Drawing Sheets

(56) References Cited

U.S. PATENT DOCUMENTS

| | | |
|---|---|---|
| 6,616,613 B1 | 9/2003 | Goodman |
| 6,997,882 B1 | 2/2006 | Parker et al. |
| 7,248,915 B2 | 7/2007 | Rönnholm |
| 7,277,749 B2 | 10/2007 | Gordon |
| 7,550,826 B2 | 6/2009 | Orth et al. |
| 7,690,253 B2 | 4/2010 | Noda et al. |
| RE41,376 E | 6/2010 | Torch |
| 7,835,529 B2 | 11/2010 | Hernandez et al. |
| 7,866,212 B2 | 1/2011 | Ariav et al. |
| 8,172,766 B1 | 5/2012 | Kayyali et al. |
| 8,193,941 B2 | 6/2012 | Wolfe et al. |
| 2002/0142811 A1 | 10/2002 | Gupta et al. |
| 2003/0088196 A1 | 5/2003 | Steve |
| 2003/0163287 A1 | 8/2003 | Vock et al. |
| 2004/0125922 A1 | 7/2004 | Specht |
| 2004/0148169 A1 | 7/2004 | Baker |
| 2004/0193003 A1 | 9/2004 | Mechlenburg et al. |
| 2005/0038647 A1 | 2/2005 | Baker |
| 2005/0065778 A1 | 3/2005 | Mastrianni et al. |
| 2005/0074055 A1 | 4/2005 | Takatori et al. |
| 2006/0224072 A1* | 10/2006 | Shennib .................. 600/509 |
| 2006/0267779 A1 | 11/2006 | Ishikawa et al. |
| 2007/0270550 A1 | 11/2007 | Perrault et al. |
| 2007/0293781 A1 | 12/2007 | Sims et al. |
| 2008/0094226 A1 | 4/2008 | O'shea et al. |
| 2008/0262381 A1 | 10/2008 | Kolen |
| 2008/0306706 A1 | 12/2008 | Markovic |
| 2009/0012786 A1 | 1/2009 | Zhang et al. |
| 2009/0131759 A1 | 5/2009 | Sims et al. |
| 2009/0147965 A1 | 6/2009 | Kuo |
| 2009/0182913 A1* | 7/2009 | Rosenblatt et al. ............. 710/72 |
| 2009/0278820 A1 | 11/2009 | Fourquin et al. |
| 2009/0315719 A1 | 12/2009 | Song |
| 2010/0052896 A1 | 3/2010 | Goodman |
| 2010/0217158 A1 | 8/2010 | Wolfe et al. |
| 2010/0217345 A1 | 8/2010 | Wolfe et al. |
| 2010/0226491 A1 | 9/2010 | Conte et al. |
| 2010/0261984 A1 | 10/2010 | Tsai et al. |
| 2010/0283618 A1 | 11/2010 | Wolfe et al. |
| 2010/0286545 A1 | 11/2010 | Wolfe et al. |
| 2010/0286567 A1 | 11/2010 | Wolfe et al. |
| 2012/0220888 A1 | 8/2012 | Wolfe et al. |

FOREIGN PATENT DOCUMENTS

| | | |
|---|---|---|
| KR | 1020000038271 | 7/2000 |
| KR | 1020050047374 | 5/2005 |
| KR | 1020060061451 | 6/2006 |
| KR | 1020060068562 | 6/2006 |

\* cited by examiner

US 8,882,677 B2

MICROPHONE FOR REMOTE HEALTH SENSING

CROSS-REFERENCE TO RELATED APPLICATIONS

This application is a divisional of U.S. patent application Ser. No. 12/392,913 filed on Feb. 25, 2009, and issued as U.S. Pat. No. 8,628,478 on Jan. 14, 2014. This application and patent are incorporated herein by reference in their entirety and for any purpose.

BACKGROUND

Several health related conditions or occurrences may have indicators that reflect a measurable factor such as motion or lack of motion. For example, for sleep apnea, a sleep disorder where an individual stops breathing for an extended period of time, the indicator is a lapse in breathing. As such, the individual's chest and/or abdomen may fail to move during this period of time. Similarly, motion may also be related to the non-breathing infant suffering from Sudden Infant Death Syndrome (SIDS). An additional example of a health related condition or occurrence relating to motion is an injury to an elderly person caused by falling.

While some indicators may reflect motion, other indicators may reflect an additional or alternative measurable factor. The most basic vital signs are pulse, blood pressure, body temperature, and respiratory rate. As discussed above, respiratory rate may reflect motion. However, while pulse is based on the motion of the heart, it is often sensed using sound sensing instruments. Blood pressure is also often sensed using a sound instrument together with a pressure cuff and body temperature is independent of motion altogether. Additionally, with respect to SIDS, an indicator of a possibly dangerous condition is when an infant is sleeping on their stomach. That is, where infants are positioned on their back when sleeping, the number of occurrences of SIDS tends to decrease. Thus, an indicator relating to SIDS may reflect a measurable factor such as the sleep position of the infant.

BRIEF DESCRIPTION OF THE FIGURES

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1:
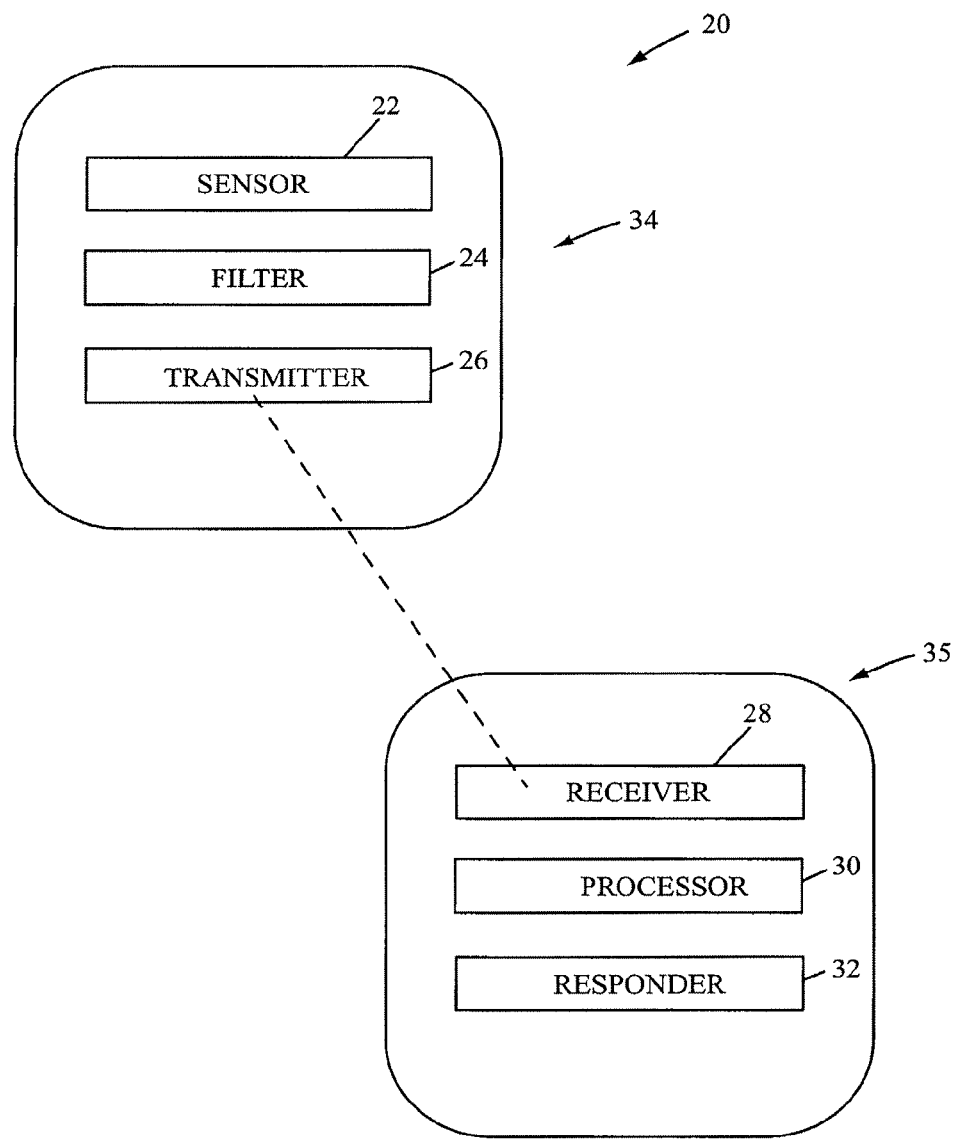
FIG. 1 is a schematic diagram of a system for monitoring indicators of health related conditions or occurrences, arranged in accordance with the present disclosure.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Monitoring indicators of health related conditions may allow certain conditions to be treated and may facilitate intervention where necessary. Additionally, monitoring the indicators may facilitate prompt response to certain health related occurrences. Manual monitoring of these indicators is generally not feasible due to the subtle nature of these indicators together with unpredictable and sometimes untimely health related conditions or occurrences.

The following detailed description relates to sensing measurable factors associated with indicators of health related conditions or occurrences and further relates to actions that may be taken in response to those measurements. The description includes discussion of sensors for sensing several measurable factors and the associated data from these sensors. The description further includes a discussion of a system that may sense the measurable factors, provide a sensor signal to a filter, filter the data from the sensor, provide a filter signal to a transmitter, and transmit an associated transmission signal. The system may also receive a transmitted signal, process the transmitted signal, and take or prompt a responsive action. For example, in the case of heart monitoring, the system may sense sound associated with a heartbeat, provide a sensor signal to a filter which may filter the result and transmit a signal continually or only when the result is indicative of a heart arrhythmia. In turn, the system may receive the transmitted signal and process the transmitted signal depending on the goals and set up of the particular system. That is, again in the case of heart monitoring, the system may process the transmitted signal by activating a stimulus to interrupt the arrhythmia or it may notify someone of the condition.

More particularly, in some examples the system may include an accelerometer type sensor adapted to sense measurable factors such as the motion or the position of a user. Alternatively, the system may include a microphone type sensor adapted to sense sound. The system may also include a filter in the form of a processor for analyzing the data from the sensor to determine if an indicator has been detected. A transmitter may also be included for transmitting a signal. The system may further include a receiver for receiving the transmitted signal and an additional processor. The additional processor may determine what type of responsive action is appropriate and may further initiate or prompt that action. These actions may include stimulating the user to interrupt an indicator episode, notifying a third party to intervene, monitoring the user, or mitigating the indicator episode. As may be appreciated, the sensor or transmitter may be provided for placement at separate locations.

Referring now to FIG. 1, a schematic diagram of a system 20 is shown, according to certain examples arranged in accordance with the present disclosure. The system 20 includes a sensor 22, a filter 24, and a transmitter 26. The system 20 also includes a receiver 28, a processor 30, and a responder 32. The sensor 22, filter 24, and transmitter 26 may be provided as a health sensing device 34 of the system and the receiver 28, processor 30, and responder 32 may be provided as a health action device 35 of the system. The health sensing device 34 and health action device 35 may be provided by the same entity or may be separately provided while being configured to communicate with each other. Also, the various functions and features of the individual functional components (e.g., 22, 23, 26, 28, 30, and 32) can be combined together into one or more integrated solutions, or separated into additional functional components as may be desired in a particular implementation.

The sensor 22 may include one or more individual sensors of any variety. In some examples, sensor 22 may be adapted to sense measurable factors reflecting indications of health related conditions or occurrences. For example, sensor 22 may be a thermometer, an automatic blood pressure sensor, a pulse sensor, or any other pressure transducer. In another example, sensor 22 may be an accelerometer. In still further examples, sensor 22 may be a microphone or an ultrasound sensor. In still another example, sensor 22 may be a rapid eye movement sensor. In yet another example, sensor 22 may be a blood sugar sensor or an air flow sensor. The type of sensor 22 used, may be based on the type of health related condition or occurrence that the system 20 is intended to address. Additionally, multiple sensors 22 may be included to address several conditions or occurrences at any given time. Additionally, several levels of sophistication may be available for each type of sensor 22. For example, several levels of precision, accuracy, and detail may be available depending on the type and quality of the sensor 22 selected for use. Moreover, the sensor 22 may provide continuous or periodic signals to the filter or the signals may be based on the circumstances of what is being sensed and what values are being sensed.

An accelerometer type sensor 22 may sense changes in velocity and thus may be used to sense motion. Such a sensor 22 may be appropriate for health related conditions such as sleep apnea, Sudden Infant Death Syndrome (SIDS), heart conditions, pregnancy, or any other health condition related to motion. As discussed briefly above, sleep apnea may be indicated by a lapse in breathing, which may cause motion of the chest and/or abdomen to stop. As such, the application of an accelerometer to the chest and/or abdomen of a person suffering from sleep apnea may allow for sensing the associated breathing patterns. Regarding SIDS, while the actual cause remains unknown, at some point, it involves a lapse in breathing and an accelerometer may be used in a similar manner as with sleep apnea. With respect to heart conditions, motions related to a heartbeat may be sensed in several locations on the human body allowing for sensing of patterns including several known arrhythmias. Regarding pregnancy, the motions associated with uterine contractions may also be appropriately sensed with an accelerometer by placing it on the surface of the abdomen thereby sensing the motion of the abdomen and, in turn, reflecting the contraction pattern of the uterus.

In addition to the health related conditions discussed above, an accelerometer may also be appropriate for health related occurrences such as falling down, blunt force trauma, or any occurrence involving a change in speed or direction. When a person falls, they may experience an initial acceleration followed by additional acceleration until they encounter the ground or other object, at which point they may experience a rapid deceleration or negative acceleration. As such, the occurrence of a fall or series of falls may be sensed by an accelerometer positioned on the body and may be particularly useful for the elderly. Similarly, an accelerometer could be used to sense occurrences related to blunt force trauma. This may be relevant for car accidents, abuse, or similar situations.

In addition to sensing motion, an accelerometer may be capable of sensing position in the absence of motion. An accelerometer may be sensitive to gravitational forces depending on its orientation relative to the surface of the earth. As such, an accelerometer may also be used to sense the position of a user where the orientation of the accelerometer is dependent on the position of the user. This may facilitate use of an accelerometer for monitoring infants for SIDS. It has been shown that infants who are positioned on their back while sleeping are less likely to be subject to SIDS. An accelerometer thus may be used to sense this sleep position by securing the accelerometer to the infant such that the orientation of the accelerometer changes as the infant's sleep position changes allowing the accelerometer to sense when the infant is face down. Alternatively, a pressure transducer could be used and the weight of the infant compressing or pressing on the sensor may be sensed to determine if the infant it face-down or face-up.

A microphone may also be used as a sensor 22 to sense sound and may be appropriate for health related conditions such as snoring, heart disease, or any other condition involving the emission of sound. Like an accelerometer, a microphone may be used to sense heartbeats from several locations on the body, allowing for sensing of patterns including several known heartbeat arrhythmias. With respect to snoring, a microphone may be used to sense the volume, frequency, pattern or any other aspect of the sound relevant to the snoring condition.

Continuing with the discussion of FIG. 1, a filter 24 may be provided and may be configured to receive a sensor signal from a single sensor 22. Alternatively, the filter 24 may be programmed to monitor several incoming sensor signals from several sensors 22 simultaneously. The sensor signal may be comprised of one or more digital signals or analog signals, which may carry data from the sensor 22 to the filter 24 for further analysis or processing. The filter 24 may range from a basic signal filter to a more sophisticated computer processor. In one example, a basic signal filter (e.g., a digital filter or an analog filter) may include a determination of whether a specific condition exists or does not exist. That is, the sensor 22 may provide one sensor signal to the filter 24 for one condition and an alternative sensor signal for another condition. The filter 24 may wait for one or the other sensor signal and then may communicate a corresponding filter signal to the transmitter 26. In some examples, a filter 24 may be omitted, for example, where the sensor 22 is adapted to provide a sensor signal only when a specific condition exists. In an alternative example, a more sophisticated filter, in the form of a processor (e.g., a digital signal processor or DSP, a microcontroller, a micro-processor, an analog signal processor, an application specific integrated circuit or ASIC, etc.), may be used to provide additional analysis of the sensor signal. That is, sensor 22 may provide a sensor signal involving a value for comparison to a threshold value defined relative to certain health related conditions discussed below. Alternatively, sensor 22 may provide a series of sensor signals to be considered together. For example, the series may define a pattern where gaps or inconsistencies in the pattern may be analyzed.

Depending on the result of any analysis conducted by filter 24, filter 24 may then communicate a filter signal (i.e., a filtered version of the signal received from sensor 22) to the transmitter 26. The filter signal may take one form or a combination of several forms. In one example, the filter signal may reflect that an indicator has been detected. In another example, the filter signal may be an indication signal together with the data received from sensor 22. In still another example, the filter signal may be an indication signal together with the data received from sensor 22 and any additional information regarding the indicating episode. In yet another example, the filter signal may be a continuous data stream reflecting the continuing values sensed by sensor 22. In still another example, the filter signal may include instructions relating to the action to be taken with respect to the several types of data. In some examples, filter 24 may be either omitted or incorporated into the sensor 22 and the filter signal may be provided by sensor 22 to transmitter 26. In still another example, the filter signal may take the form of a continuous or periodically sent beacon signal for assuring that communication has not been lost due to reduced proximity, power loss, or other conditions. For example, the filter may periodically produce a filter signal indicating that it is operating properly and within communications range. Optionally, the processor may first receive a sensor signal from the sensor 22 and determine that the sensor reading indicates a safe health condition before sending such a signal.

In the case of sleep apnea, the filter 24 may receive a sensor signal from the sensor 22 reflecting the breathing pattern of a user. The sensor signal may have gaps where the user pauses between breaths. The filter 24, in this example, may be a processor capable of timing the length of the gaps and comparing the length of the gap to a threshold value. A gap in breathing that exceeds approximately 10 to 20 seconds may be considered an apnea. Alternatively, other lengths of time may be used and may be customized to a user. As such, the processor may communicate a filter signal to the transmitter 26 when a selected threshold value is exceeded. The filter signal may be an indication signal reflecting a likelihood that an apnea has occurred. In another example, the filter signal may be an indication signal together with the data relating to the breathing pattern surrounding the apnea. In another example, the filter signal may also include data relating to the apnea such as how long breathing lapsed, how many apneas per hour are occurring, and the like.

The above described process may also be performed by the filter 24 when an infant is being monitored for the breathing related aspects of SIDS. However, where the infant is being monitored for the sleep position aspects of SIDS, the filter 24 may have alternative functionality. The filter 24 may receive a sensor signal from the sensor 22 reflecting the sleep position of the infant (for example, acceleration values due to gravity in an X, Y, and/or Z axis). This may be a signal with a varying scale or it may be a signal reflecting that the infant is on his/her back or on his/her stomach. In one example, the Z axis acceleration value may be nominally 1 G when the infant is on his or her back and nominally −1 G when the infant is on his/her stomach. Such a Z axis value may be compared to a threshold, for example −0.8 G, to provide an indication that the infant is likely in an unsafe position. Where the sensor 22 is limited to a sensor signal reflecting that the infant is on his/her back or stomach, the filter 24 may be configured to do nothing unless and until the sensor signal is received reflecting that the infant is on his/her stomach or has been for some threshold period of time. At that point, the filter 24 may communicate a filter signal to the transmitter. This example may be simplified where the sensor 22 does not send a sensor signal unless the infant is on his/her stomach. In that example, the filter 24 may be configured to initiate a filter signal to the transmitter 26 when the filter 24 receives a sensor signal from the sensor 22. Alternatively, the filter 24 may be eliminated and the sensor 22 may send a sensor signal to the transmitter 26. In the above examples, the signal (whether a filter signal or a sensor signal) sent to the transmitter 26 may take several forms and may include several levels of data. This may be dependent on the level sophistication of both the sensor 22 and the filter 24 and further dependent on the goals associated with using the system. Additionally, the sensor 22 may be able to be calibrated periodically or each time it is used. That is, the sensor 22 may be positioned on an infant, the infant may be positioned on his/her back and the system may then be informed that this reflects a safe condition. This could occur via pushing a recalibration button or other mechanism. Having informed the system, the current gravitational force on the sensor may be a benchmark for measuring the position of the infant.

In the case of falls, the filter 24 may receive a sensor signal from the sensor 22 reflecting the level of force being experienced by the user. In some examples, this level of force may be in comparison to that of gravity and thus may be presented as a certain number or fraction of G forces or G's. In some other examples, the level of fall may be based on a physiological model including an analysis of peak acceleration, total energy, and direction. As such, when the sensor signal reflects that the G force has exceeded a threshold limit or the model reflects a certain level of likelihood of fall or injury, the filter 24 may communicate a filter signal to the transmitter 26. In some examples, the filter signal may be an indication that a fall has likely occurred. In other examples, the filter may be more specific and may define the fall as meeting a certain level. That is, a low level may indicate likelihood of fall, or light fall. An intermediate level may indicate a higher likelihood of fall, or medium fall. A high level may indicate a high likelihood of fall, or hard fall. In each, level, a specific response may apply. As such, the filter signal may be adapted accordingly. In additional examples, the filter signal may include additional data relating to the level of G force experienced and may include some data regarding the history of falls.

The filter 24 may have a similar role in uses of the system for monitoring heart conditions. The filter 24 may receive a sensor signal from the heart sensor and may be programmed to recognize several known heart arrhythmias or may be a more basic filter limited to recognizing only life threatening heart conditions. In either case, the filter may be configured to respond to known heart arrhythmias based on specific instructions related to each or more generic instructions related to all arrhythmias. Having recognized a heart arrhythmia or other known problem, the filter 24 may communicate a filter signal to the transmitter. In some examples, the filter 24 may continually send a filter signal to the transmitter with the results received by the sensor 22 and also continue to monitor the sensor signal from the sensor 22 for problems.

Similarly, with respect to contractions during pregnancy, the filter 24 may receive a sensor signal from a contraction sensor and may interpret the data with respect to frequency and/or magnitude. In this example, while high frequency and/or high magnitude may trigger the filter 24 to communicate a filter signal to the transmitter 26, the filter 24 may also send a continuous filter signal to the transmitter reflecting the continuing data and thus the contraction pattern received from the contraction sensor.

In alternative examples, the filter 24 may also be adapted for use in monitoring or treating snoring. In these examples, the filter 24 may receive a sensor signal from a sound sensor and may measure the decibel level of the sound to determine if it exceeds a threshold level. As discussed with respect to other conditions, this example may also include sending a range of possible filter signals to the transmitter 26 including an indication of snoring, the decibel of the snoring, and/or a continuous signal reflecting the snoring pattern. In some examples, the filter may also receive a sensor signal from a motion sensor or other sensor positioned on or around a sleep partner. In this example, the sensor positioned on or around the sleep partner may be adapted to sense sleep partner irritation. As such, the filter, in this example, may be adapted to rely on both the sound sensor and the motion sensor to determine what action to take. That is, if the snoring is loud or continuous, the filter may send a filter signal to the transmitter to trigger a sound canceling device or to trigger a stimulation device. Additionally, the filter may receive information from the motion sensor as to the irritation level of the sleep partner. As such, when the snoring is not loud or continuous or otherwise clearly bothersome, the filter may still send a filter signal to the transmitter to trigger a sound canceling device or to trigger a stimulation device. In another example, however, the filter may not send a filter signal to the transmitter if no sound is being detected or the sound is really low. That is, if the sleep partner is just restless, a filter signal may not be sent.

With continued reference to FIG. 1, the transmitter 26 of the system may include any known device for transmitting information. This may include any wired transmitter or wireless transmitter. The transmission may be in digital or analog form and may be a radio transmission or other type of transmission. As such, any suitable radio transmitter, low voltage communication device such as a lower power digital radio, a wireless device, or any communication device known in the art may be used. In some examples, this may be a radio packet, short distance communication system. In other examples, the transmitter may be adapted for longer distance communication. One suitable radio transmitter may be an ANT11TS63M4IB low-powered digital radio developed by Dynastream Innovations Inc., of Cochrane, Alberta, Canada.

Accordingly, the receiver 28 of the system may also be any known device for receiving information. The receiver 28 may be chosen to correlate with the type of transmitter 26 used. As such, the receiver 28 may include any wired receiver or wireless receiver. Moreover, the receiver 28 may be adapted to receive the transmission from the transmitter 26 and communicate the associated information to the processor 30 with a receiver signal. The transmitter may include an antenna of any variety. In one example, the antenna may be a strip-line antenna. In other examples the antenna may be a coil type antenna.

Still referring to FIG. 1, the processor 30 may receive the transmitted signal from the receiver 28. As with the filter 24, the processor 30 may have a range of sophistication depending on the goals and needs of the system. As such, the processor 30 may be triggered by the receiver signal to complete a single specific task. In this example, having received a receiver signal, the processor 30 may drive a device in response. In other examples, the processor 30 may separate the incoming transmitted data into categories relating to the action to be taken. That is, some of the data may be intended for storage or display, some may be intended to trigger a stimulus, notification, or mitigation response, and some may require interpretation prior to moving on to these tasks. As such, the processor 30 may perform several tasks corresponding to the form of the data it receives and the actions that need to be taken. In the case of a beacon signal being sent by the filter to ensure that communication has not been lost, where the beacon signal is not received, the processor may track the amount of time that has passed and trigger an alarm or other notification when a threshold amount of time has been exceeded. Such a notification may be unique to not receiving the beacon signal. It may include telephoning a pre-programmed number and leaving a message indicating that contact with sensor has been lost.

Concluding the discussion of FIG. 1, the responder 32 may include several options for devices adapted to respond to the information gathered by the sensor 22. The responder 32 may include a database for storing the data for later analysis. The responder 32 may also include a display for displaying the data for real time analysis or monitoring. In one example, the responder 32 is a stimulation device for stimulating the user, while in another example, the responder 32 may be a notification device for notifying a third party. In still another example, the responder 32 may be a mitigating device for mitigating a given situation.

For example, the responder 32 may include a computer with a graphics display and a hard drive or other database structure. Alternatively, a stimulation device in the form of a vibratory or alarm type device may be included. Alternatively, a similar device may be included to notify a third party. The notification device may include a light up display, alarm, or vibratory device. Alternatively, the notification may involve sending an additional signal in the form of a message to a remote monitoring device via a traditional computer network such as Wi-Fi, Bluetooth, or Ethernet, via a telephony network, or via a dedicated radio link. For example, a text message may be sent to a parent's or monitoring person's cellular phone when an alert condition is detected. Alternatively, a mitigating device may include any device adapted to assist a user or other person in coping with a health condition or occurrence.

In the case of sleep apnea, a non-breathing episode may be interrupted by a stimulus which arouses a user sufficiently for them to begin breathing again. Alternatively, a notification may be provided to a third party. In the case of SIDS, a parental monitor may be activated to notify the parent of a life threatening or otherwise potentially dangerous condition such as a non-breathing infant or an infant that has rolled onto his/her stomach. In the case of heart conditions, the responder 32 may include a device for stimulating the user and may go the extent of actually shocking their heart to attempt to correct an arrhythmia. In this or another example, the responder 32 may include a database for storing a continuous stream of heartbeat history. This may also include a continual display of the heartbeat on a computer display or other display to allow the heart to be monitored. In the case of a user who has fallen, the responder 32 may include a notification device for notifying a nurse at the user's nursing home, or a family member, that assistance may be needed. In the case of snoring, a stimulation similar to that discussed above regarding apnea may be included. In another example, a mitigation device such as a sound cancellation device may be used to cancel out the sound of the snoring in an effort to comfort those around the snoring person.

Figure 2:
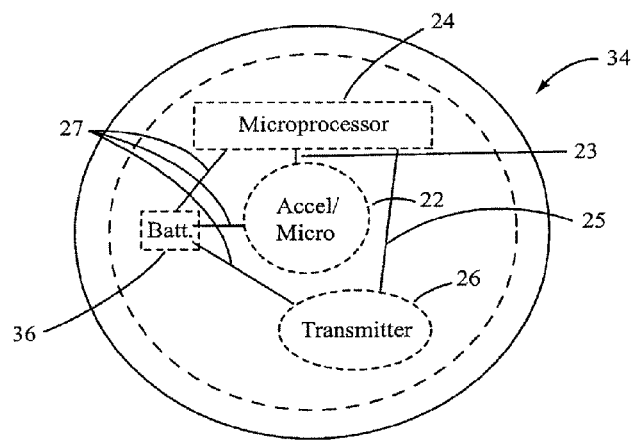
FIG. 2 is a top schematic view of the components of a health sensing device, arranged in accordance with the present disclosure.

Referring now to FIG. 2, one example of a health sensing device 34 is shown. The device 34 includes a sensor 22, a filter 24, and a transmitter 26 and thus includes three elements of the system shown in FIG. 1. In alternative examples, more or fewer elements may be provided. In the present example, the sensor 22 may be an accelerometer, microphone, and/or any reasonable combination of previously described sensors. Also in the present example, the filter 24 may be a microprocessor and the transmitter 26 may be a radio transmitter. Additionally shown is a power source 36 (e.g. a battery) for powering the several elements of the health sensing device 34. Those skilled in the art will understand and appreciate that other sensors 22, filters 24, and transmitters 26 described herein or otherwise may also be used in a health sensing device 34 like the one described here and are thus within the scope of the present disclosure.

In the example shown in FIG. 2, the sensor 22 may be connected to the filter 24 with an information bus 23 for carrying information sensed by the sensor 22 in the form of a sensor signal to the filter 24. Additionally, the filter 24 may be connected to the transmitter 26 with an additional information bus 25 for carrying information to the transmitter 26 in the form of a filter signal. The power source 36 may be included to power one or several of the included elements and may be connected to each of the elements 22, 24, and 26 as shown with a power wire or cord 27. In an alternative embodiment, the power source only powers the filter 24, which in turn powers the sensor 22 and the transmitter 26 by including power in conjunction with the data buses 23 and 25. The power source 36 may be a battery or series of batteries and may be capable of being turned on and off. In one example, the battery is a zinc based battery and may be a Zinc/Air battery. In other examples, the battery may be a Lithium-ion based battery, a Nickel Cadmium based battery, or a Nickel Metal Hydride.

The example of FIG. 2, may include a substrate for positioning of the elements of the health sensing device. The substrate may be a flat and/or flexible material for securing the elements of the device. As such, the substrate may include a silicon based substrate, a ceramic based substrate, a glass type substrate, a quartz type substrate or any other reasonable substrate material. In some examples, the substrate may be a high-performance plastic such as polyimide or Polyetheretherketone (PEEK) film. In other examples, polyester may be used, for instance with silver screen printed circuits. In other examples, a variety of potting materials may be used such as an epoxy resin. The substrate may also include an enclosing structure. This enclosing structure may be in the form of a patch and may include a shielding structure. For example, in the case of a radio frequency transmitter and/or receiver, the patch may include a shielding structure to prevent radio frequency interference (RFI). The patch may be a relatively soft flexible material or it may be a more rigid material. The patch may be made from several materials including, but not limited to nylon, cotton, plastic or any other material appropriate for use in contact with the body or clothing. The material of the patch may be waterproofed with a coating or be naturally waterproof. Depending on the nature of the patch (e.g. flexible or rigid) the elements of the device may be enclosed within the patch in an envelope type structure or the elements may be provided on the surface of a substrate. In one example, the elements of the device are provided on the surface of a silicon based substrate, the substrate further including an enveloping waterproofed nylon material in the form of a patch. In light of the present disclosure, several orientations of the elements within the patch will be apparent to those of skill in the art when consideration is given to electrical connections between the elements and physical placement within the patch. Moreover, depending on the type of sensor 22 and the condition for which it is being used, the sensor 22 may be located near the surface of the patch that is located adjacent to the user so as to minimize relative movement, or other interference, between the surface of the user and the sensor 22.

Figure 3:
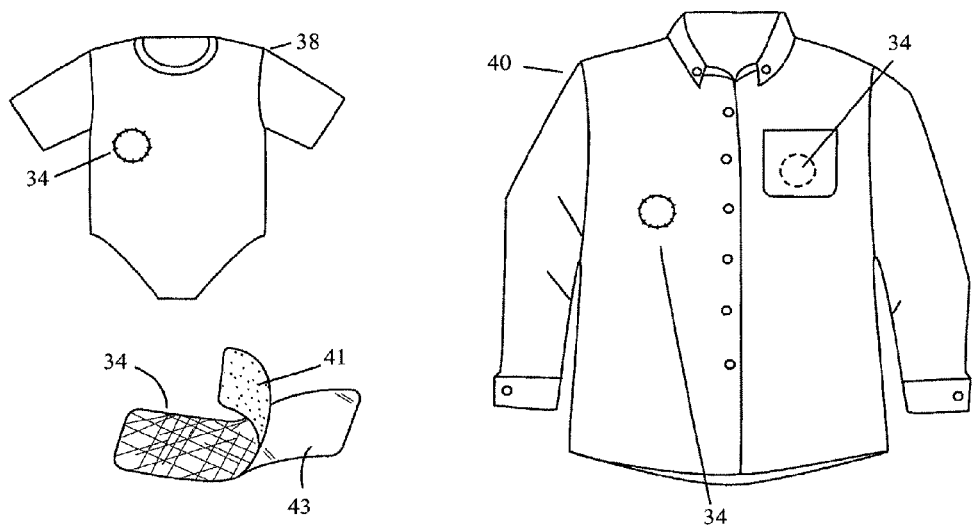
FIG. 3 is a diagram of a health sensing device incorporated into clothing, arranged in accordance with the present disclosure.

Referring now to FIG. 3, the patch may have an affixing element such as a peel and stick bottom surface 41 for adhering the patch to a user, where a protective layer 43 over the adhesive may be removed prior to applying the patch. In one example, the patch may include a bio-adhesive for securing the patch directly to the skin of a user. This bio-adhesive may have an adhesive value so as to make removal difficult. That is, in the case of infants or elderly users who may suffer from dementia or otherwise have a tendency to remove the device, the patch may be securely affixed to the user and not be easily removed. In one example, the patch may be located in a hard to reach location to make removal difficult. Alternatively, the affixing element may be an attachment surface for repeated application such as a hook and loop surface with a complementary hook and loop surface worn by the user. In still another example, the affixing element may include self securing straps for wrapping around a portion of a user's body for securing the patch between the straps and the surface of the user's body. The straps may have several openings for receiving corresponding protrusions for adjustability or may be self-secured with buttons, hook and loop, buckles, or other means known in the art.

Referring to FIG. 3, in another example, the affixing element of the health sensing device 34 may be adapted to incorporate the device 34 into clothing. In some examples, the device 34 may be configured substantially as shown and described with respect to FIG. 2. In one example, the device 34 may be sewn or otherwise affixed to baby clothing 38 such as a sleeper, a shirt, a one size body suit or other attire worn by a baby. The device 34 may be sewn to the back or front of the clothing depending on its configuration and what it is designed to sense. In another example, the patch may be sewn or otherwise affixed to adult clothing 40. In light of the present disclosure, those skilled in the art will understand and appreciate that the health sensing device 34 may be otherwise secured to clothing through the use of buttons, fabric glue, or other methods known for fastening devices to clothing. In some examples, the health sensing device 34 may not be fixedly secured, but may be placed in a pocket of a shirt or other clothing article.

The sensors or other elements of the present disclosure may be micro-electro-mechanical systems (MEMS) devices. That is they may incorporate integrated circuit technology with microfabrication in the form of micromachining. For example, a sensor may be an LIS302DL MEMS motion sensor manufactured by STMicroelectronics. Alternatively, the sensors or other elements may be made from more or less sophisticated technologies.

Figure 4:
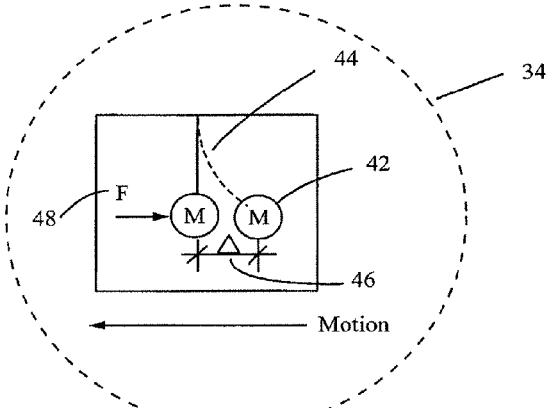
FIG. 4 is a schematic diagram of an accelerometer, arranged in accordance with the present disclosure.

The accelerometer disclosed herein may sense motion associated with the user. Referring to FIG. 4, a schematic diagram of the functionality of an accelerometer within a health sensing device 34 is shown. Generally, an accelerometer functions by monitoring the affect on a mass 42 suspended within the accelerometer when accelerated. That is, the mass 42 is held in place with a deflectable resistance 44. When the accelerometer is moved, the mass 42 tends to stay in place causing deflection 46 in the deflectable resistance 44. A deflection measurement and the known properties of the deflectable resistance 44 allows for the calculation of the force 48 required to cause that deflection 46. Together with the defined mass 42, this force can be used to calculate an acceleration. Where the accelerometer is affixed to a user, the acceleration of the accelerometer may be assumed to match that of the user.

The accelerometer may be secured within a health sensing device 34 to minimize the effect of relative motion between the accelerometer and the user. In this regard, where the health sensing device 34 is flexible, the accelerometer may be located near the affixing surface. Where a relatively rigid device is used and the accelerometer is secured therein, more options for the location of the accelerometer may be available. In various examples, the accelerometer may take the form of a basic spring based accelerometer, an E-transformer accelerometer, or any other accelerometer. The accelerometer may be designed and calibrated based on a specific health condition. In cases of small accelerations, such as heartbeats and contractions, a relatively sensitive accelerometer may be used. In contrast, where falls or sudden involuntary motions are being monitored, a relatively less sensitive accelerometer may be used.

Figure 5:
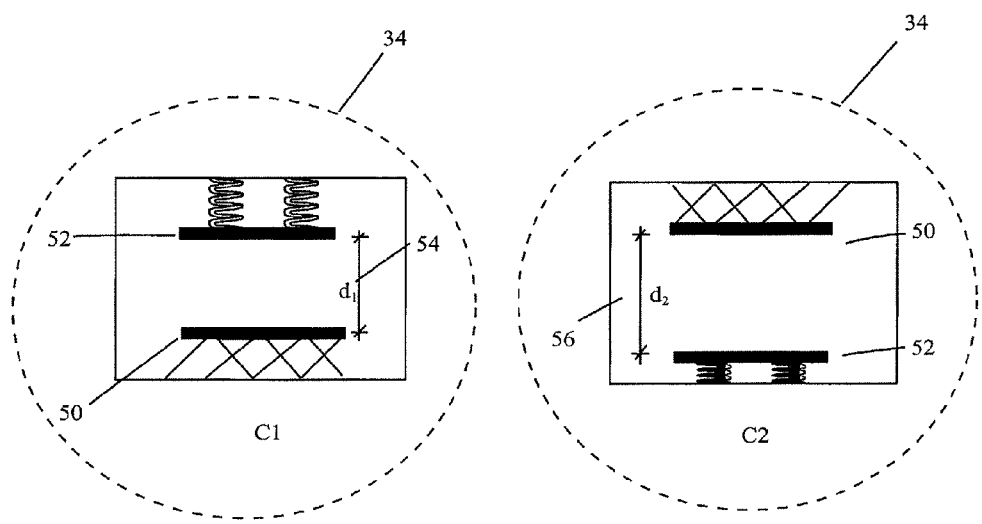
FIG. 5 is a schematic diagram of a capacitor based accelerometer, arranged in accordance with the present disclosure.

Referring to FIG. 5, the accelerometer within the health sensing device 34 may take the form of a variable capacitance device. Capacitors are generally described as devices that store energy in an electric field between a pair of conductor plates. The capacitance value of a capacitor may be affected by several factors, such as the area and materials of the conductive plates, the distance between the conductive plates, and a dielectric value associated with the gap between the conductive plates. As used herein, the variable capacitance device may sense motion or orientation by having a conductor plate spacing that varies depending on the orientation or motion of the device. As such, the capacitor may be affixed to a user causing the orientation or motion of the user to affect the capacitance value of the variable capacitance device.

For example, the variable capacitance device may be designed with two plates spaced apart from each other. In one example, one of the plates may be a rigidly supported plate 50 and the other plate may be a flexibly supported plate 52 positioned above the rigidly supported plate 50. When the device is in an upright position (e.g., rigidly supported plate 50 on the bottom, flexibly supported plate 52 on the top) the device may have a first capacitance value, C1, that is determined by a first distance 54, d1, between the plates 50 and 52. However, when the device is in the inverted position (e.g., rigidly supported plate 50 on the top, flexibly supported plate 52 on the bottom), the force of gravity causes the flexibly supported plate 52 to move away from the rigidly supported plate 50 causing the device to have a second capacitance value, C2, that is different from the first capacitance value, C1. Since the distance 56, d2, between the plates 50 and 52 is greater in the inverted position than in the upright (or non-inverted) position, and since capacitance value is inversely proportional to the distance between the plates, the second capacitance value (C2) will be smaller than the first capacitance value (C1). In light of the present disclosure, those of skill in the art will understand and appreciate that the orientation of the conductor plates 50, 52 could be reversed such that the upright position is defined by the flexibly supported plate 52 being below the rigidly supported plate 50.

The variable capacitance device may be designed and calibrated with respect to a specific health condition. For example, in the case of SIDS, where the concern relates to an infant rolling from their back to their stomach, an acceleration shift from 1 G to −1 G is reflected. As such, the sensitivity may be relatively low. That is, the support for the flexibly supported plate 52 may be relatively stiff. However, where a similar device is also being used to sense breathing or other relatively small accelerations, the sensitivity may be relatively high. That is, the support for the flexibly supported plate 52 may be relatively flexible. Those skilled in the art will understand and appreciate that several known and later developed accelerometer designs may be appropriate for use in the devices described herein.

Similarly, the microphone disclosed herein may be a micro-electro-mechanical systems (MEMS) microphone. As such, the microphone may take the form of a variable capacitance circuit with a capacitance value determined by the spacing between a diaphragm and a back plate. Sound, which generally can be described as a moving air pressure wave, can cause the diaphragm to vibrate such that the capacitance value changes in the circuit due to changing position of the diaphragm relative to the back plate. The sound may thus be transformed into an electrical signal via the variable capacitance circuit. Alternatively, the microphone may be an electret condenser type of microphone (ECM).

Figure 6:
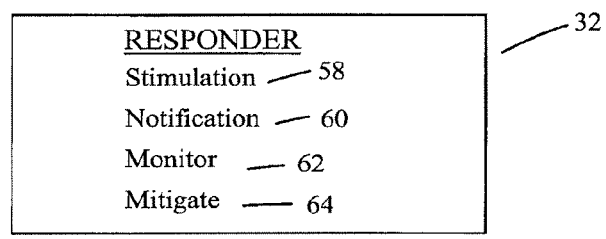
FIG. 6 is a schematic diagram of actions taken in response to a signal, in accordance with the present disclosure.

Referring now to FIG. 6, the responder 32 of a system as described with respect to FIG. 1 may include a stimulation device 58, a notification device 60, monitoring/storage device 62, a mitigation device 64, or any combination of these devices.

Regarding the stimulation device 58, several health conditions may lend themselves toward this action. For example, sleep apnea, SIDS, heart conditions, contractions, diabetes, snoring, and falling may all be appropriately corrected, at least temporarily, by stimulating the user. For the conditions relating to breathing, several methods of stimulation may be used such as sounding an alarm, a tone, or other audible stimuli in close proximity to the user. Alternatively, a vibratory or other mechanical stimulus may be used. In the case of heart arrhythmias, these audible or mechanical agitation methods may be sufficient to arouse the patient and correct a minor arrhythmia. However, in some examples, the stimulus may involve shocking the user in an attempt to correct the arrhythmia. In the case of contractions, the stimulus may actually be an injection or other dosing intended to prevent further contractions. Regarding diabetes, a stimulus similar to those described for breathing conditions may be sufficient to arouse a diabetic suffering from low blood sugar allowing them to correct the deficiency. Regarding falling, a device proximally located to the user may include a stimulation to the user triggering them to tell a monitoring party that they are O.K. That is, where the level of acceleration sensed by the sensor is relatively low, a device proximally located to the user may light up or otherwise notify the user that their device has indicated a fall. As such, if they are not in need of assistance they may notify a third party that no assistance is needed. In one example, this may be positioned on the health sensing device positioned on the user. This example may also include a button or other actuatable element allowing the user to notify the third party that they are O.K. by pushing the button or other actuatable element. Those skilled in the art will understand and appreciate that several known stimuli may be appropriate for stimulating users suffering from these and other types of conditions and these stimuli are thus within the scope of the present disclosure.

Regarding the notification device 60, several health related conditions or occurrences may lend themselves toward this action. For example, falling, heart conditions, and SIDS may lend themselves to this type of action. An elderly person in a nursing home may require assistance from staff after a fall. A light on a light board or in the hallway may be activated to trigger the staff. Alternatively, a notification on a computer screen may be provided. Similarly, a user suffering from a heart condition may need hands on support to correct a heart arrhythmia or myocardial infarction. As such, similar notifications may be made to hospital staff, family members, or even an emergency response service. In the case of SIDS, whether breathing has stopped or the infant has rolled onto their stomach, a notification of parents may be appropriate. This may be in the form of sounding an alarm or other notification. Those of skill in the art will understand that several devices for notifying others are known and are thus within the scope of the present disclosure. These may include pagers, computers, cell phones using text messages, and other notification devices known in the art.

Regarding storing/monitoring devices 62, many of the conditions may be appropriate for this action. That is, in most cases, a history may be relevant to analyzing a condition, occurrence, or series of occurrences. As such, one action may involve storing the sensed data, or the existence of a condition or occurrence for later reference and analysis. Additionally, a continuous display may be appropriate for live monitoring and analysis of a given condition.

Regarding mitigation devices 64, this may be appropriate where an indicating episode is not being prevented or stopped, but rather is simply being coped with. That is, in the case of snoring, a sound cancellation device may be used to model the snoring and send out a canceling signal so as to minimize the disruption of a sleep partner of a snoring person. Additionally, a mitigation action may be appropriate where pain is associated with the indicating episode and thus medicine may be dispensed to minimize the pain suffered by a user.

Figure 7:
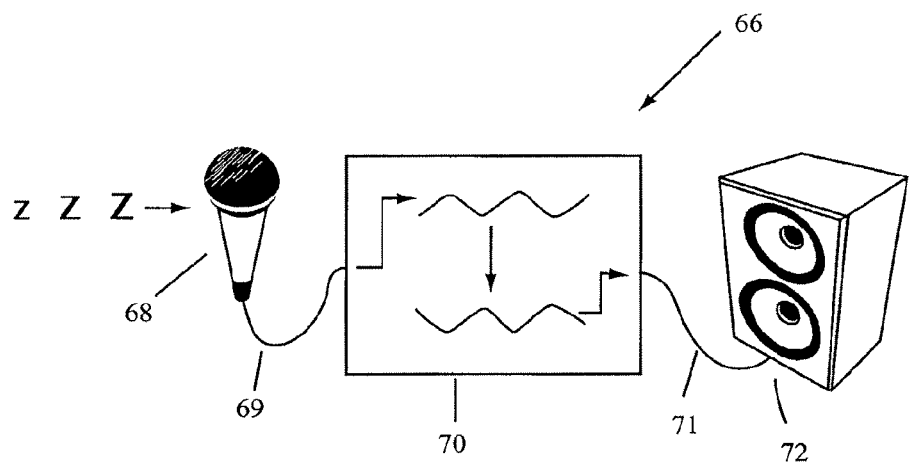
FIG. 7 is a schematic diagram of a method of sound cancellation, in accordance with the present disclosure.

Referring now to FIG. 7, a diagram of a sound cancelling mitigation device 66 is shown. As shown, a microphone 68 may receive a snoring sound from a snorer. An inverse waveform generator 70 with an inverting amplifier may receive the sound wave from the microphone 68 via an information bus 69. The inverse wave form generator 70, together with the inverting amplifier may create an inverse waveform and may send that wave form to a speaker 72 via an information bus 71. The speaker 72 may then broadcast a sound cancelling signal making the snoring sound less apparent. As such, the affect of the snoring sound on others around the snorer may be minimized. Further discussion regarding cancellation signals may be found in patent application Ser. No. 12/400,488 entitled Noise Cancellation in Cell Phone Conversation, filed on Mar. 9, 2009, the contents of which are hereby incorporated by reference herein.

Figure 8:
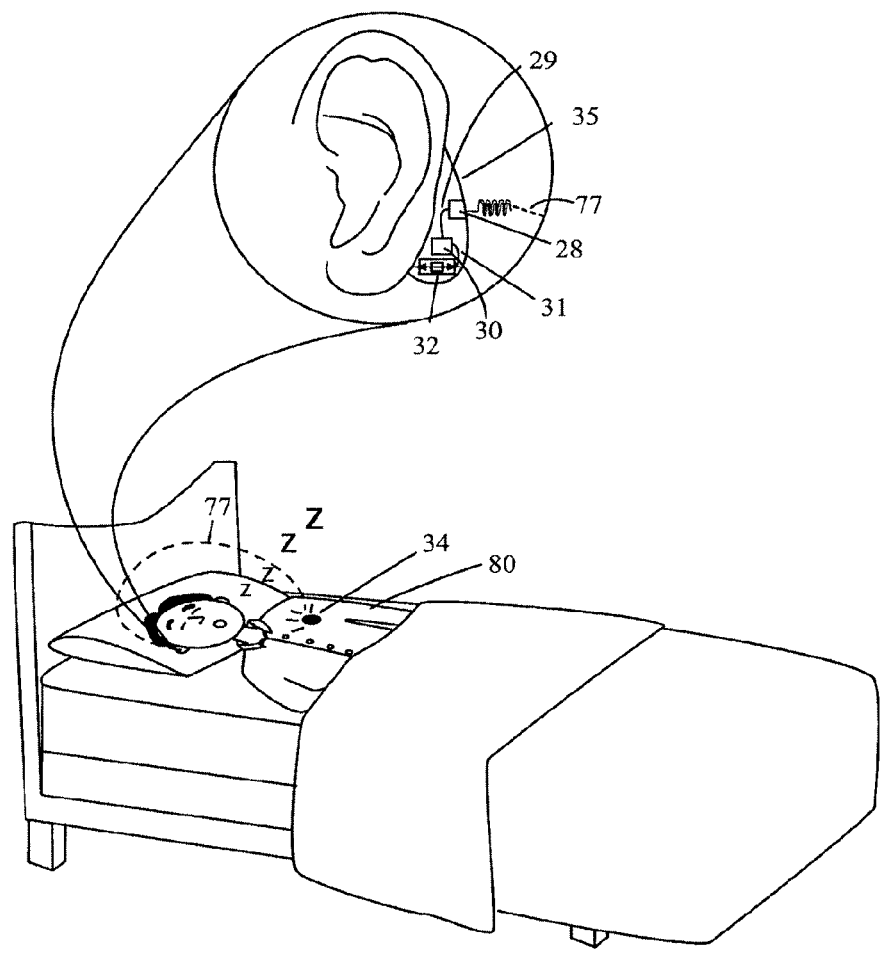
FIG. 8 is a diagram of a health sensing device adapted to monitor a user for snoring, in accordance with the present disclosure.

Referring now to FIG. 8, the health sensing device 34 may be used to monitor a snoring user 80. In FIG. 8, a user 80 is shown with a health sensing device 34 in the form of a patch affixed to their chest. In this example, the device 34 may be a microphone based device intended to sense sound and as such may be affixed anywhere it will reasonably pick up snoring sounds. This may be on the chest as shown, but could also be on the neck, arm, or other bodily location, or otherwise located off of the body of the user. When the user 80 begins to snore, snore loudly, snore continuously, or otherwise exceed a threshold, the device 34 may transmit a signal to a health action device 35 allowing the user 80 to be stimulated by a vibratory or alarm type stimulus causing the user 80 to stop the snoring. Alternatively, the device 34 may transmit a signal to a health action device 35 allowing a mitigating sound cancellation device to be activated so as to minimize the affect on the users sleep partner. As shown, the health sensing device described in FIG. 2 may sense snoring and transmit a transmission signal 77 to a health action device 35. The health action device 35 may take the form of an ear piece adapted to accommodate the user's ear. The device 35 may include a receiver 28, a processor 30 and a responder 32. As with the health sensing device, the receiver 28 may be connected to the processor with an information bus 29 for carrying information from the receiver 28 to the processor 30 in the form of a receiver signal. The processor may be connected to the responder 32 with an information bus 31 for carrying information from the processor to the responder in the form of a responder signal. In the present example, the health sensing device 34 may transmit a signal indicative of a snoring event to the health action device 35. The receiver 28 of the health action device 35, may then send a signal to the processor 30, which may, in turn, drive the responder 32. In the present example, the responder may take the form of a vibratory device intended to arouse the user 80 sufficiently to stop breathing.

Figure 9:
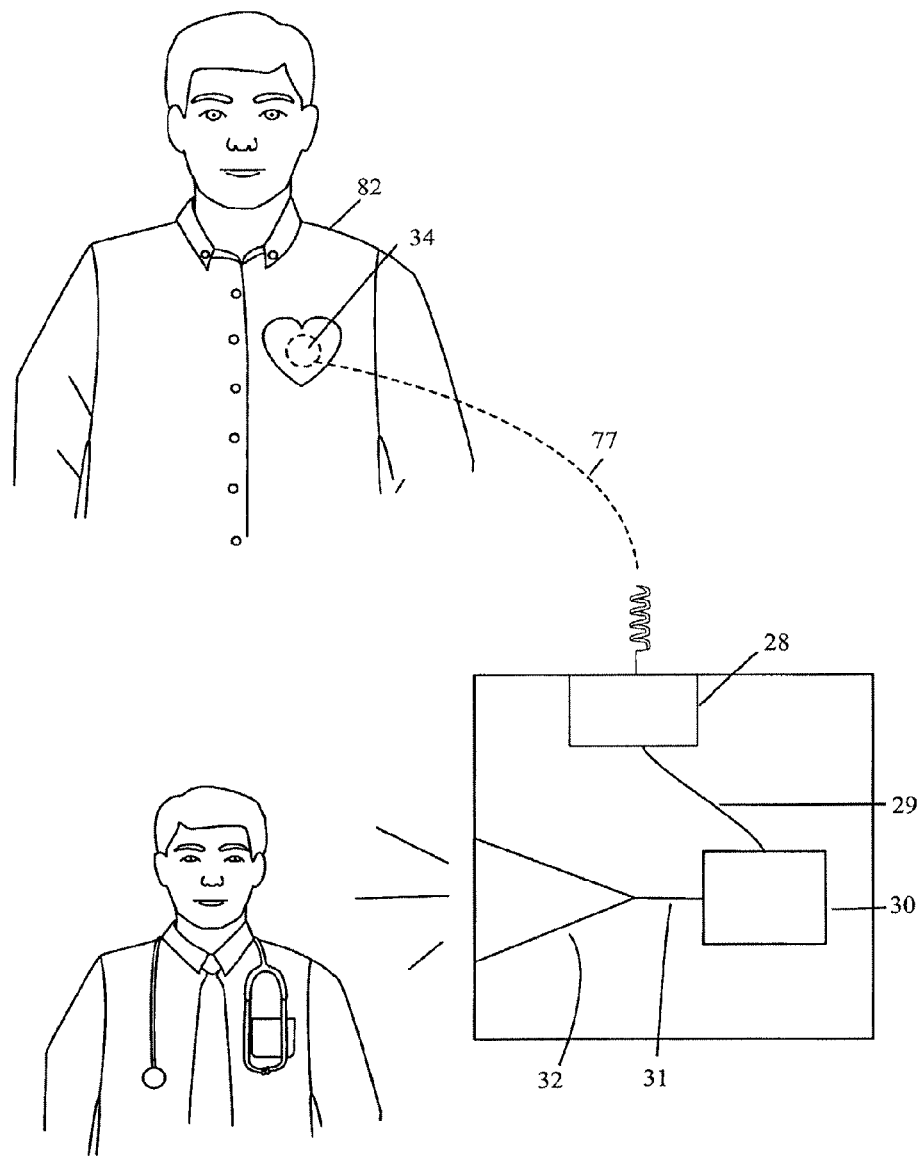
FIG. 9 is a diagram of a health sensing device adapted to monitor the heartbeat of a user, in accordance with the present disclosure.

Referring now to FIG. 9, a health sensing device 34 may be used to monitor the heartbeat of a user 82. In FIG. 9, a user 82 is shown with a health sensing device 34 in the form of a patch affixed to their chest. In this example, the device 34 may be a microphone based device intended to sense heartbeat sounds and monitor heart rhythms. As such, it may act as a remote stethoscope and may be located anywhere on the body where heartbeat sounds may be heard. When the user 82 suffers an arrhythmia or other abnormal heartbeat condition, the device 34 can detect the heartbeat condition and transmit a signal to a health action device 35 to notify hospital staff, family members, or emergency response teams to come to the aid of the user 82. As shown, the health sensing device described in FIG. 2 may sense a heart arrhythmia and transmit a transmission signal 77 to a health action device 35. The health action device may include a receiver 28, a processor 30 and a responder 32. As with the health sensing device, the receiver 28 may be connected to the processor with an information bus 29 for carrying information from the receiver 28 to the processor 30 in the form of a receiver signal. The processor may be connected to the responder 32 with an information bus 31 for carrying information from the processor to the responder in the form of a responder signal. In the present example, the health sensing device 34 may transmit a signal indicative of a heart condition to the health action device 35. The receiver 28 of the health action device 35, may then send a signal to the processor 30, which may, in turn, drive the responder 32. In the present example, the responder may take the form of an audio alarm intended to notify on site personnel of a heart condition of the user 82.

Other uses may be apparent to those of skill in the art. These uses may include, but are not limited to, monitoring sleep apnea, SIDS, elderly falls, and sleep partner irritation as discussed in the following patent applications with the following titles and filing dates, the content of which are all hereby incorporated by reference herein:

Accelerometer Based Health Sensing, filed May 6, 2009 and assigned U.S. application Ser. No. 12/436,615, and published as U.S. Publication No. 2010/0286545 A1 on Nov. 11, 2010;

Sudden Infant Death Syndrome Prevention Clothing, filed on Feb. 25, 2009 and assigned U.S. application Ser. No. 12/392,889, and published as U.S. Publication No. 2010-0217158 on Aug. 26, 2010;

Elderly Fall Protection, filed May 6, 2009 and assigned U.S. application Ser. No. 12/436,462 and published as U.S. Publication No. 2010/0286567 A1 on Nov. 11, 2010, now abandoned; and Snoring Treatment, filed May 6, 2009 and assigned U.S. application Ser. No. 12/436,550, and published as U.S. Publication No. 2010/0283618 A1 on Nov. 11, 2010, and issued as U.S. Pat. No. 8,193,941 on Jun. 5, 2012.

Figure 10:
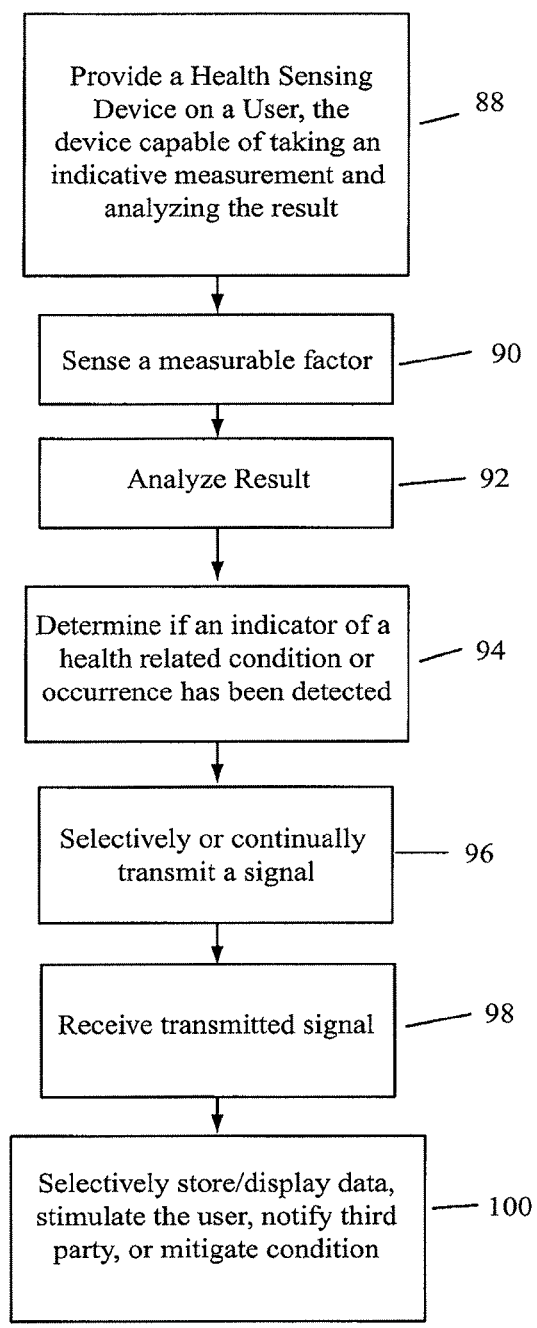
FIG. 10 is a diagram of a method of monitoring indicators of a health related condition or occurrence, in accordance with the present disclosure.

FIG. 10 is a diagram of a method of monitoring indicators of a health related condition or occurrence. The method includes providing a health sensing device capable of taking an indicative measurement and analyzing the result 88. The method further includes sensing a measurable factor 90, analyzing the result 92, and determining if an indicator of a health related condition or occurrence has been detected 94. The method may also include selectively or continually transmitting a signal 96 and receiving the transmitted signal 98. The method may also include storing/displaying the data, stimulating the user, notifying a third party, or providing mitigation 100.

In the present method, a health sensing device 34 as discussed with respect to FIGS. 1-6 may be used. Sensing a measurable factor 90 may be performed by a sensor 22. In addition, analyzing the result and determining if an indicator of a health related condition or occurrence has been detected 94, may be performed by a filter 24. Selectively or continually transmitting a signal and receiving the transmitted signal may each be performed by a respective transmitter 26 and receiver 28. Decisions regarding what action to take may be performed by a processor 30 and the additional step 100 may be performed by a responder 32.

Figure 11:
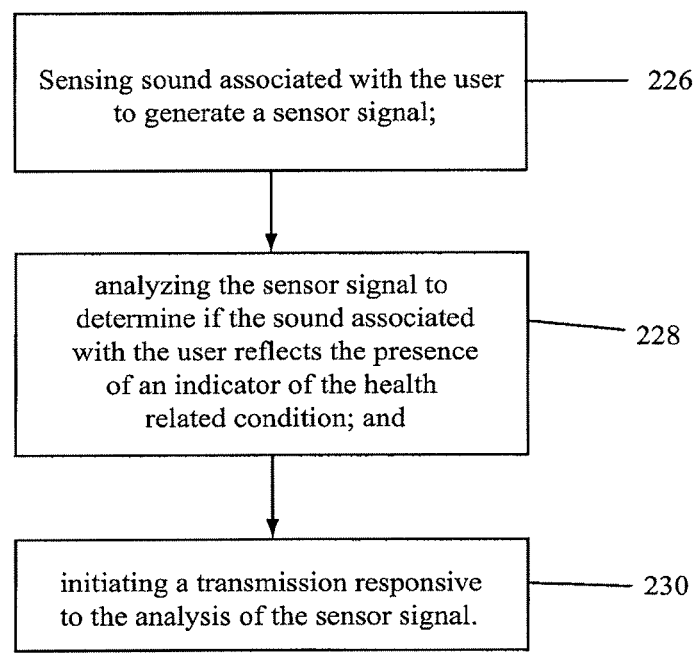
FIG. 11 is a diagram of a method of monitoring a user for a health related condition, in accordance with the present disclosure.

Referring to FIG. 11, a method for a health sensing device to monitor a user for a health related condition is shown. The method may include sensing sound associated with the user to generate a sensor signal 226, analyzing the sensor signal to determine if the sound associated with the user reflects the presence of an indicator of the health related condition 228, and initiating a transmission responsive to the analysis of the sensor signal 230.

In the present method, a health sensing device 34 as discussed with respect to FIGS. 1-6 may be used. Sensing sound associated with the user to generate a sensor signal 226 may be performed by a sensor 22 in the form of a microphone. Analyzing the sensor signal to determine if the sound associated with the user reflects the presence of an indicator of the health related condition 228 may be performed by a filter 24, whereas initiating a transmission responsive to the analysis of the sensor signal 230 may be performed by a transmitter 26.

Figure 12:
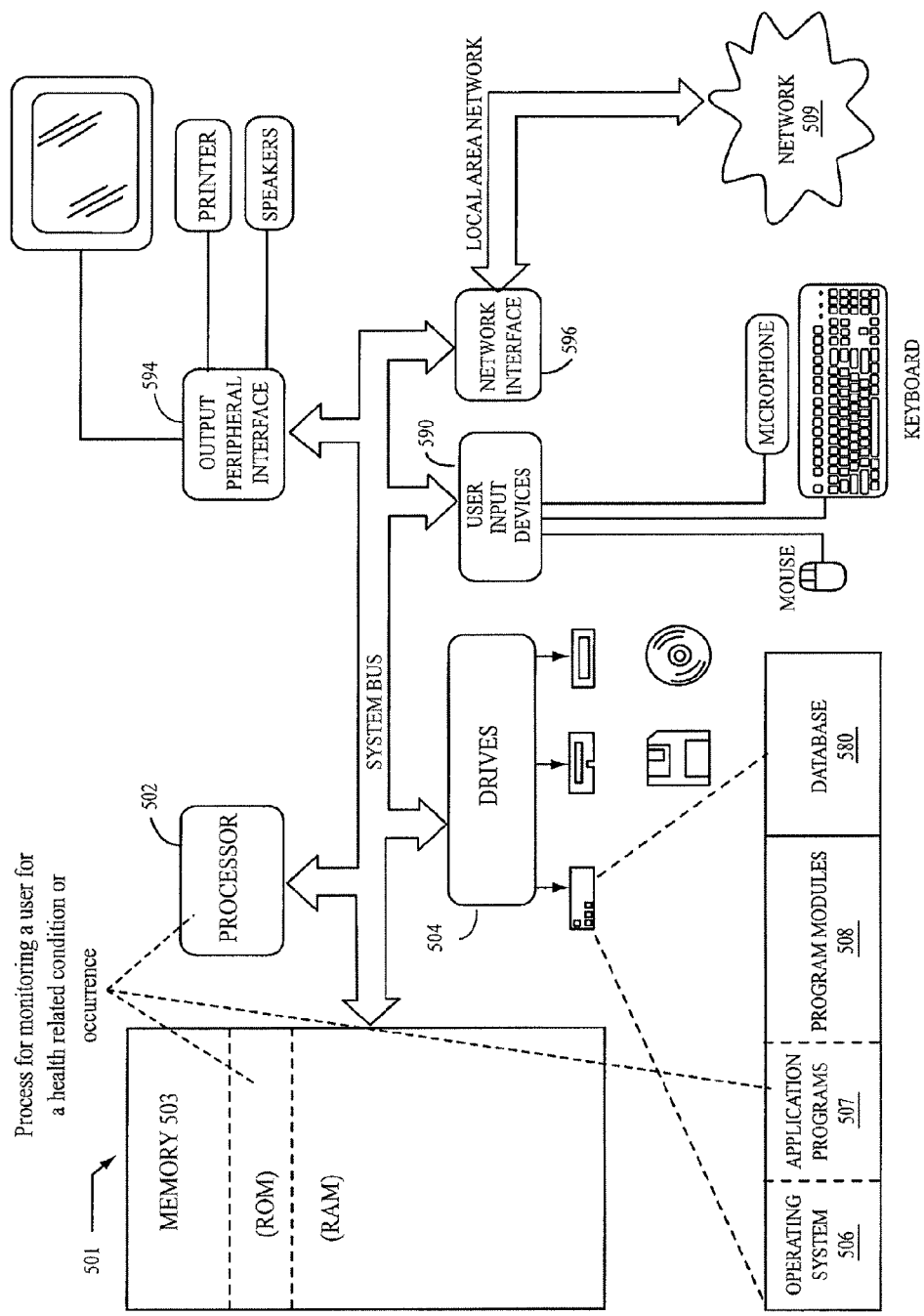
FIG. 12 is a diagram of a computing system arranged in accordance with some examples of the present disclosure.

Any or all of the elements of the health sensing device or health action device may be provided in a computer environment. For examples, the filter of the health sensing device or the processor of the health action device may be provided in a computer environment. In other examples, the health sensing device and/or the health action device may be provide in a computer environment. As shown in FIG. 12, the computing system includes a computer 501, including a central processing unit (CPU), also referred to as a processor, 502, main memory 503 and one or more bulk storage devices 504. The processor 502 can generally be of any desired configuration including but not limited to a microprocessor ($\mu P$), a microcontroller ($\mu C$), a digital signal processor (DSP), or any combination thereof. Thus, each processor 502 can include logic for executing program instructions as well as other functional blocks such as an arithmetic logic unit (ALU), a floating point unit (FPU), a digital signal processing (DSP) core, registers, accumulators, etc. The main memory 503, which may be any suitable form of memory including, but not limited to, volatile memory such as random access memory (RAM), non-volatile memory such as read only memory (ROM) and flash memory storage, data storage devices such as magnetic disk storage (e.g., hard disk drive or HDD), tape storage, optical storage (e.g., compact disk or CD, digital versatile disk or DVD), or other machine-readable storage mediums that can be removable, non-removable, volatile or non-volatile.

The bulk storage devices 504 and their associated computer storage media provide storage of computer readable instructions, data structures, program modules and other data for the computer 501. The bulk storage devices 504 can also include an operating system 506, application programs 507, program modules 508, and a database 580. The computer 501 further includes user input devices 590 through which a user may enter commands and data. Input devices can include an electronic digitizer, a microphone, a keyboard and pointing device, commonly referred to as a mouse, trackball or touch pad. Other input devices may include a joystick, game pad, satellite dish, scanner, or the like.

These and other input devices can be connected to the processor 502 through a user input interface that is coupled to a system bus, but may be connected by other interface and bus structures, such as a parallel port, game port or a universal serial bus (USB). Computers such as computer 501 may also include other peripheral output devices such as speakers, which may be connected through an output peripheral interface 594 or the like.

The computer 501 may operate in a networked environment using logical connections to one or more computers, such as a remote computer connected to network interface 596. The remote computer may be a personal computer, a server, a router, a network PC, a peer device or other common network node, and can include many or all of the elements described above relative to computer 501. The remote computer may be considered the other of the client or the server depending on the designation of the computer 501. Networking environments are commonplace in offices, enterprise-wide area networks (WAN), local area networks (LAN), intranets and the Internet. Source and destination machines need not be connected by a network 509 or any other means, but instead, data may be migrated via any media capable of being written by the source platform and read by the destination platform or platforms. When used in a LAN or WLAN networking environment, the computer 501 is connected to the LAN through a network interface 596 or an adapter. When used in a WAN networking environment, computer 501 typically includes a modem or other means for establishing communications over the WAN, such as the Internet or network 509. It will be appreciated that other means of establishing a communications link between the computers may be used.

Those skilled in the art will understand and appreciate that several modifications may be made to the examples disclosed herein and that the result will still be within the scope of the present disclosure. Moreover, those of skill in the art will understand and appreciate that additional uses beyond those described are within the scope of the present disclosure.

For example, the device may be adapted to monitor restless leg syndrome, seizures, or Tourette's syndrome. Restless leg syndrome may be monitored for accelerations exceeding normal accelerations experienced while sleeping. Similarly, Tourette's syndrome users and those users suffering from seizures may be monitored for accelerations exceeding those normally experienced in every day life. Those of skill in the art will understand and appreciate that several other health related conditions are directly or indirectly related to motion and application of a health sensing device to these conditions is thus within the scope of the present disclosure.

Those skilled in the art will understand and appreciate that depending on the organization and proximity of the devices disclosed herein, the transmission step may not be necessary. As such, the filter and the processor may be combined in to a single filter/processor. Additional combinations and organizations of the elements of the system will be apparent to those of skill in the art.

The foregoing describes various examples of health sensing. Following are specific examples of methods, devices, and systems of health sensing. These are for illustration only and are not intended to be limiting. In one example, a health sensing device for placement on a user may include a microphone configured to monitor a factor relating to an indicator of a health related condition or occurrence and generate a sensor signal in response to the monitored factor, a filter configured to receive the sensor signal, determine if the indicator has been detected, and generate a filter signal when the indicator is detected, and a transmitter configured to receive the filter signal and generate a transmission responsive to the filter signal. In another example, the factor is sound. In another example, the indicator is an irregular heartbeat. In another example, to determine if the indicator has been detected, the filter is configured to recognize a heart arrhythmia. In another example, a health sensing system may include the above device and a second device including a receiver and a processor wherein the processor is configured to notify a third party. In another example, the processor is configured to stimulate the user.

In another example, a method for a health sensing device to monitor a user for a health related condition may include sensing sound associated with the user to generate a sensor signal, analyzing the sensor signal to determine if the sound associated with the user reflects the presence of an indicator of the health related condition, and initiating a transmission responsive to the analysis of the sensor signal. In another example, initiating the transmission includes selectively transmitting when the indicator is present. In another example, the method may also include encoding the transmission signal with information including a determination of whether the indicator is present. In another example, the method may also include receiving the transmission and performing a process. In another example, performing a process includes stimulating the user with a stimulating device. In another example, performing a process includes notifying a third party. In another example, initiating the transmission includes continually transmitting a signal. In another example, the method may also include encoding the transmission with data reflecting the sound of the user and further comprising receiving the transmission and storing the data.

In another example, a health action device for responding to an indicator of a health related condition or occurrence of a user may include a receiver configured to receive a transmission from a transmitter on a health sensing device and communicate a receiver signal to a processor, a processor configured to receive the receiver signal, interpret the receiver signal, and communicate a processor signal to a responder, and a responder configured to receive the processor signal and conduct an action responsive to the health related condition. In another example, the action includes notifying a third party. In another example, the responder is an audio alarm and notifying a third party includes sounding the alarm. In another example, the processor signal includes instructions responsive to the health related condition. In another example, the instructions relate to treatment of a heart arrhythmia. In another example, the responder is a shocking device adapted to shock the user according to the instructions.

The present disclosure is not to be limited in terms of the particular examples described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.), It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A method for a health sensing device to monitor a user for a health related condition, comprising:
    sensing with a microphone sound associated with the user snoring to generate a sensor signal;
    analyzing the sensor signal to determine if the sound associated with the user snoring reflects the presence of an indicator of the health related condition; and
    initiating a transmission responsive to the analysis of the sensor signal.

2. The method of claim 1, wherein initiating the transmission includes selectively transmitting when the indicator is present.

3. The method of claim 2, further comprising encoding the transmission signal with information including a determination of whether the indicator is present.

4. The method of claim 3, further comprising receiving the transmission and performing a process.

5. Tile method of claim 3, wherein performing a process includes stimulating the user with a stimulating device.

6. The method of claim 3, wherein performing a process includes notifying a third party.

7. The method of claim 1, wherein initiating the transmission includes continually transmitting a signal.

8. The method of claim 7, further comprising encoding the transmission with data reflecting the sound of the user snoring and further comprising receiving the transmission and storing the data.

9. The method of claim 1, wherein sensing sound associated with the user snoring to generate a sensor signal comprises sensing sound generated by a snoring of the user.

10. The method of claim 1, further comprising affixing a flexible patch including a microphone to the user, and wherein sensing sound associated with the user snoring to generate a sensor signal comprises sensing the sound with the microphone.

11. A health action device for responding to an indicator of a health related condition or occurrence of a user, the device comprising:
    a receiver configured to receive a transmission from a transmitter on a health sensing device, wherein the health sensing device is configured to sense sound associated with the user snoring with a microphone, and communicate a receiver signal to a processor;
    a processor configured to receive the receiver signal, interpret the receiver signal, and communicate a processor signal to a responder; and
    a responder configured to receive the processor signal and conduct an action responsive to the health related condition.

12. The device of claim 11, wherein the action includes notifying a third party.

13. The device of claim 12, wherein the responder is an audio alarm and notifying a third party includes sounding the alarm.

14. The device of claim 11, wherein the processor signal includes instructions responsive to the health related condition.

15. The device of claim 14, wherein the instructions relate to treatment of a heart arrhythmia.

16. The device of claim 15, wherein the responder is a shocking device adapted to shock the user according to the instructions.

17. The device of claim 11, wherein the health sensing device comprises a flexible patch.

* * * * *

UNITED STATES PATENT AND TRADEMARK OFFICE
CERTIFICATE OF CORRECTION

| | | |
|---|---|---|
| PATENT NO. | : 8,882,677 B2 | Page 1 of 1 |
| APPLICATION NO. | : 14/030884 | |
| DATED | : November 11, 2014 | |
| INVENTOR(S) | : Wolfe et al. | |

It is certified that error appears in the above-identified patent and that said Letters Patent is hereby corrected as shown below:

On the Title Page, Item (71), under "Applicant", in Column 1, Line 1, delete "Development," and insert -- Development --, therefor.

On the Title Page, Item (62), in Column 1, Line 2, delete "2009." and insert -- 2009, now Pat. No. 8,628,478. --, therefor.

In the Specification

In Column 1, Line 7, delete "divisional of" and insert -- divisional application under 35 U.S.C. § 121 of --, therefor.

In Column 14, Line 60, delete "Protection," and insert -- Detection, --, therefor.

In Column 18, Line 23, delete "etc.)," and insert -- etc.). --, therefor.

In the Claims

In Column 20, Line 1, in Claim 5, delete "Tile" and insert -- The --, therefor.

Signed and Sealed this
Twelfth Day of May, 2015

Michelle K. Lee
*Director of the United States Patent and Trademark Office*